United States Patent
Perrone, Jr. et al.

(10) Patent No.: US 8,105,386 B2
(45) Date of Patent: Jan. 31, 2012

(54) ROTATING/NON-ROTATING TIBIA BASE PLATE/INSERT SYSTEM

(75) Inventors: Charles H. Perrone, Jr., Austin, TX (US); Aaron A. Hofmann, Salt Lake City, UT (US); James William Burrows, Austin, TX (US)

(73) Assignee: Zimmer, Inc., Warsaw, IN (US)

( * ) Notice: Subject to any disclaimer, the term of this patent is extended or adjusted under 35 U.S.C. 154(b) by 265 days.

(21) Appl. No.: 10/771,887

(22) Filed: Feb. 4, 2004

(65) Prior Publication Data

US 2004/0215345 A1 Oct. 28, 2004

Related U.S. Application Data

(60) Provisional application No. 60/444,817, filed on Feb. 4, 2003.

(51) Int. Cl.
*A61F 2/38* (2006.01)
(52) U.S. Cl. ..................................... 623/20.29
(58) Field of Classification Search ............... 623/22.37, 623/23.53, 13.12–13.2, 20.14–20.36
See application file for complete search history.

(56) References Cited

U.S. PATENT DOCUMENTS

| | | | | |
|---|---|---|---|---|
| 4,016,606 A | * | 4/1977 | Murray et al. | 623/20.21 |
| 4,257,129 A | * | 3/1981 | Volz | 623/20.33 |
| 4,538,305 A | * | 9/1985 | Engelbrecht et al. | 623/20.25 |
| 4,714,474 A | * | 12/1987 | Brooks et al. | 623/20.33 |
| 4,759,767 A | * | 7/1988 | Lacey | 623/20.34 |
| 4,822,362 A | * | 4/1989 | Walker et al. | 623/20.32 |
| 4,883,488 A | * | 11/1989 | Bloebaum et al. | 623/20.34 |
| 5,062,852 A | * | 11/1991 | Dorr et al. | 623/20.33 |
| 5,071,438 A | * | 12/1991 | Jones et al. | 623/20.29 |
| 5,108,442 A | * | 4/1992 | Smith | 623/20.33 |
| 5,358,531 A | * | 10/1994 | Goodfellow et al. | 623/20.29 |
| 5,405,398 A | * | 4/1995 | Buford et al. | 623/20.27 |

(Continued)

FOREIGN PATENT DOCUMENTS

EP 0 809 986 A2 12/1997

(Continued)

OTHER PUBLICATIONS

PCT Search Report from PCT/US2004/003065 dated Jun. 6, 2004.

(Continued)

*Primary Examiner* — David Isabella
*Assistant Examiner* — Ann Schillinger
(74) *Attorney, Agent, or Firm* — Baker & Daniels LLP (57) ABSTRACT

The present invention is directed to a rotating/non-rotating tibia base plate/insert system. In one illustrative embodiment, the device comprises a tibia base plate, an insert adapted to be positioned above the base plate, and at least one removable pin that, when installed, engages at least a portion of the insert and the base plate to thereby prevent relative rotation between the insert and the base plate. In one illustrative embodiment, the method comprises obtaining a prosthetic knee assembly comprised of a tibia base plate, a tibia insert and a removable pin, the assembly being adapted to be configured in a first state such that the tibia insert may rotate relative to the base plate or in a second state such that said tibia insert cannot rotate relative to said base plate, making at least one incision adjacent a patient's knee, installing the prosthetic knee assembly in the patient, wherein the removable pin is removed such that the assembly is in the first state wherein the tibia insert may rotate relative to the tibia base plate, and closing the incision.

21 Claims, 7 Drawing Sheets

U.S. PATENT DOCUMENTS

| | | | | |
|---|---|---|---|---|
| 5,413,605 A * | 5/1995 | Ashby et al. | | 623/20.34 |
| 5,413,608 A * | 5/1995 | Keller | | 623/20.33 |
| 5,480,445 A * | 1/1996 | Burkinshaw | | 623/20.32 |
| 5,489,311 A * | 2/1996 | Cipolletti | | 623/20.34 |
| 5,554,158 A | 9/1996 | Vinciguerra et al. | | 606/80 |
| 5,658,344 A * | 8/1997 | Hurlburt | | 623/20.19 |
| 5,683,469 A * | 11/1997 | Johnson et al. | | 623/20.32 |
| 5,702,464 A * | 12/1997 | Lackey et al. | | 623/20.32 |
| 5,824,103 A | 10/1998 | Williams | | 623/20 |
| 5,871,543 A * | 2/1999 | Hofmann | | 623/20.32 |
| 5,951,603 A * | 9/1999 | O'Neil et al. | | 623/20.33 |
| 6,010,534 A * | 1/2000 | O'Neil et al. | | 623/20.34 |
| 6,074,424 A | 6/2000 | Perrone, Jr. et al. | | 623/20 |
| 6,126,692 A | 10/2000 | Robie et al. | | |
| 6,139,581 A * | 10/2000 | Engh et al. | | 623/20.34 |
| 6,162,254 A * | 12/2000 | Timoteo | | 623/20.33 |
| 6,210,444 B1 * | 4/2001 | Webster et al. | | 623/20.33 |
| 6,238,434 B1 | 5/2001 | Pappas | | |
| 6,245,110 B1 * | 6/2001 | Grundei et al. | | 623/20.31 |
| 6,299,646 B1 * | 10/2001 | Chambat et al. | | 623/20.33 |
| 6,306,172 B1 * | 10/2001 | O'Neil et al. | | 623/20.15 |
| 6,428,577 B1 * | 8/2002 | Evans et al. | | 623/20.29 |
| 6,620,168 B1 | 9/2003 | Lombardo et al. | | 606/88 |
| 6,645,215 B1 | 11/2003 | McGovern et al. | | 606/102 |
| 6,660,039 B1 * | 12/2003 | Evans et al. | | 623/20.29 |
| 2004/0186584 A1 * | 9/2004 | Keller | | 623/20.24 |

FOREIGN PATENT DOCUMENTS

| | | |
|---|---|---|
| EP | 0 809986 | 12/1997 |
| EP | 0 978 261 A1 | 2/2000 |
| EP | 0 978261 | 2/2000 |
| FR | 2 712 178 | 11/1993 |
| FR | 2271178 | 5/1995 |

OTHER PUBLICATIONS

Buechel-Pappas Tricompartmental Knee System, Surgical Technique and Brochure, ENDOTEC, 2006.

* cited by examiner

ROTATING/NON-ROTATING TIBIA BASE PLATE/INSERT SYSTEM

PRIORITY CLAIM

Applicants hereby claim priority based upon U.S. Provisional Patent Application Ser. No. 60/444,817, filed Feb. 4, 2003, entitled "Rotating Tibial Baseplate/Insert System," the entirety of which is hereby incorporated by reference.

BACKGROUND OF THE INVENTION

1. Field of the Invention

The present invention is generally related to the field of orthopedic prostheses, and, more particularly, to a rotating/non-rotating tibia base plate/insert system.

2. Description of the Related Art

The two largest and longest bones of the human body, the femur and tibia, meet at a person's knee. The tibia is situated at the front and inner side of the lower leg. The head of the tibia is large and expanded on each side into two eminences, the tuberosities. These eminences form two smooth concave compartments or surfaces which articulate with the condyles of the femur. The medial condyle is more prominent anteriorly and broader both in the anterior-posterior and transverse diameters than the lateral condyle. Accordingly, the lateral articular surface of the tibia is longer, deeper and narrower than the medial articular surface of the tibia. The medial articular surface is broader, more circular, and concave from side to side. The anterior surfaces of the tuberosities are continuous with one another, forming a single large surface which is somewhat flattened. Posteriorly, the tuberosities are separated from each other by a shallow depression for the attachment of ligaments. The medial tuberosity presents posteriorly a deep transverse groove for the insertion of a tendon.

Because of aging and disease, the articulating surfaces of the knee may degrade. To treat certain pathologies, it has become common to attach a prosthetic device to the femur and a prosthetic device to the tibia. The tibia prosthesis typically comprises a base plate that is affixed to an upper, resected surface of a tibia and an articulating surface or insert which pivots about an axis within the medial condylar compartment. Tibia prostheses commonly comprise metal base plates with polyethylene articulating surfaces mounted thereon. To accommodate the range of motion of the human knee, either the femoral condyles or a femoral prosthesis rocks against the articulating surface of the tibia prosthesis.

There are many variations that a surgeon must deal with when installing a prosthetic knee assembly. For example, due to a variety of factors, the loadings exerted on an artificial knee joint may vary greatly from person to person. Such variations may be the result of physical variations in the structure of patient's knee, previous injuries, weight, etc. In some cases, it may be desirable that the tibia insert rotate relative to the tibia base plate. It is believed that such rotation allows the artificial knee to absorb some variable loadings produced on the knee joint by the patient during everyday activities. Moreover, allowing the tibia insert to rotate relative to the tibia base plate may enable such a prosthetic system to be used on a vast variety of patients. However, in some cases, it may be desirable to prevent the tibia insert from rotating relative to the tibia base plate. For example, if the various ligaments that support the knee are weak or have been previously damaged, allowing rotation of the tibia insert relative to the tibia base plate may create an unstable knee. In a worst case scenario, allowing such rotation may lead to failure of the knee joint under some loading conditions.

In view of the foregoing, it would be desirable for a surgeon to have greater flexibility as it relates to deciding whether to use a rotating or a non-rotating tibia insert on a tibia base plate. However, the decision to use a rotating or non-rotating insert may not be finally made until some point during the process of the surgery. That is, the final decision may be based upon an inspection of the surrounding ligaments and other factors that may lead the surgeon to decide on a rotating or a non-rotating tibia insert. As a result, hospitals maintain inventories of both rotating and non-rotating insert/tibia base plate combinations to accommodate both situations. Additionally, in some cases, it may be desirable or necessary to go from a rotating tibia insert to a non-rotating insert and vice versa. For example, a patient may originally obtain a prosthetic knee system with a tibia insert that rotates relative to the tibia base plate. Over a period of time, it may be desirable to have that patient use a prosthetic knee system in which the tibia insert does not rotate relative to the base plate. With prior art systems, this would typically involve major surgery to remove the existing insert/base plate system and replace it with the other type of insert/base plate system, i.e., to go from a rotating system to a non-rotating system. Obviously, such situations involved major surgery, which patients might be reluctant to endure. Thus, patients would continue to use the previously obtained insert/base plate assembly despite the fact that a better prosthetic knee assembly may be available.

The present invention is directed to various devices and methods for solving, or at least reducing the effects of, some or all of the aforementioned problems.

SUMMARY OF THE INVENTION

The present invention is directed to a rotating/non-rotating tibia base plate/insert system. In one illustrative embodiment, the device comprises a tibia base plate, an insert adapted to be positioned above the base plate, and at least one removable pin that, when installed, engages at least a portion of the insert and the base plate to thereby prevent relative rotation between the insert and the base plate.

In another illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate.

In yet another illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate, wherein the pin has a head that is positioned adjacent a bottom surface of the base plate.

In a further illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate, wherein the pin has a shoulder that is positioned adjacent a top surface of the base plate.

In still a further illustrative embodiment, the device comprises a tibia base plate, the plate having an opening formed in a side surface of the base plate, an insert adapted to be positioned above the base plate, the insert having an opening formed on a side surface of the insert, and at least one removable pin that, when installed, prevents relative rotation between the insert and the base plate, wherein a first portion of the pin is configured to engage the opening formed in the side surface of the base plate and a second portion of the pin is configured to engage the opening formed in the side surface of the insert.

In yet a further illustrative embodiment, the device comprises a tibia base plate, an insert adapted to be positioned above the base plate, and a removable means for preventing relative rotation between the insert and the base plate. In some embodiments of the present invention, the removable means for preventing relative rotation between the insert and the base plate comprises at least one removable pin that, when installed, engages at least a portion of the insert and the base plate to thereby prevent relative rotation between the insert and the base plate.

In one illustrative embodiment of the present invention, the method comprises obtaining a prosthetic knee assembly comprised of a tibia base plate, a tibia insert and a removable pin, the assembly being adapted to be configured in a first state such that the tibia insert may rotate relative to the base plate or in a second state such that said tibia insert cannot rotate relative to said base plate, making at least one incision adjacent a patient's knee, installing the prosthetic knee assembly in the patient, wherein the removable pin is removed such that the assembly is in the first state wherein the tibia insert may rotate relative to the tibia base plate, and closing the incision.

In another illustrative embodiment, the method comprises obtaining a prosthetic knee assembly comprised of a tibia base plate, a tibia insert and a removable pin, the assembly being adapted to be configured in a first state such that the tibia insert may rotate relative to the base plate or in a second state such that said tibia insert cannot rotate relative to said base plate, making at least one incision adjacent a patient's knee, installing the prosthetic knee assembly in the patient, wherein the removable pin is left in place such that the assembly is in the second state wherein the tibia insert cannot rotate relative to the tibia base plate, and closing the incision.

In yet another illustrative embodiment, the method comprises providing a tibia base plate having a removable pin positioned in an opening formed in the tibia base plate, positioning the tibia base plate on a tibia of a patient, and positioning a tibia insert above the tibia base plate, wherein at least a portion of the removable pin is positioned in an opening formed in the tibia insert to thereby prevent relative motion between the tibia insert and the tibia base plate.

In a further illustrative embodiment, the method comprises providing a tibia base plate having a removable pin positioned in an opening formed in the tibia base plate, positioning the tibia base plate on a tibia of a patient, positioning a tibia insert above the tibia base plate and, before or after the tibia base plate is positioned on the tibia of the patient, removing the removable pin to thereby allow relative motion between the tibia insert and the tibia base plate.

In yet a further illustrative embodiment, the method comprises providing a tibia base plate having an opening formed in a side surface of the tibia base plate, positioning the tibia base plate on a tibia of a patient, positioning a tibia insert above the tibia base plate, the tibia insert having an opening formed in a side surface of the tibia insert, and positioning at least a portion of a removable pin in the opening in the side surface of the tibia base plate and another portion of the removable pin in the side surface of the tibia insert to thereby prevent relative motion between the tibia insert and the tibia base plate.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with medical-related, system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase. Various anatomical reference terms used herein are intended to have the standard meaning for such terms as understood in the medical community. For example, the application may include reference to the following terms: anterior (the front, as opposed to the posterior); posterior (the back or behind, as opposed to the anterior); inferior (below, as opposed to superior); superior (above, as opposed to inferior); lateral (toward the left or right side of the body, as opposed to medial); medial (in the middle or inside, as opposed to lateral); proximal (toward the beginning, as opposed to distal); and distal (further from the beginning, as opposed to proximal).

In general, the present invention is directed to a rotating/non-rotating tibia base plate/insert system, and methods of using same. As will be recognized by those skilled in the art after a complete reading of the present application, the present invention may be employed with a variety of prosthetic knee systems. Thus, the particular tibia inserts and tibia base plates depicted herein should not be considered a limitation of the present invention, unless such limitations are expressly set forth in the appended claims.

Figure 1:
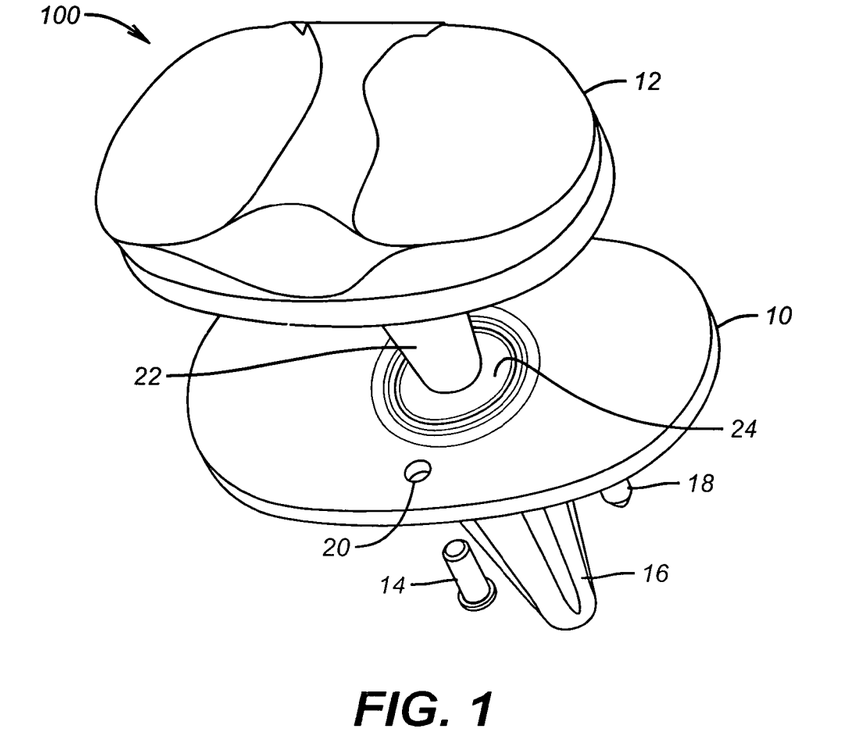
FIG. 1 is an exploded view of an insert/tibia base plate system in accordance with one embodiment of the present invention.
Figure 2:
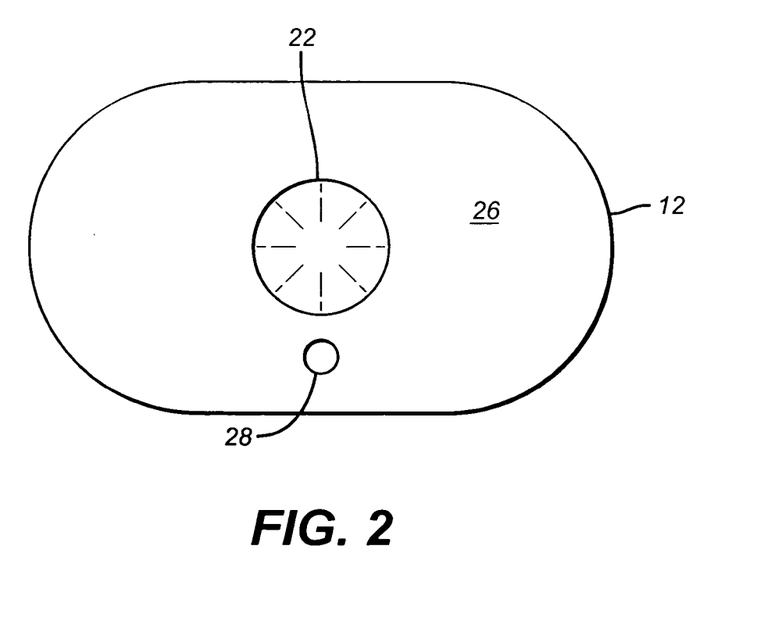
FIG. 2 is a bottom view of the insert depicted in FIG. 1.
Figure 3:
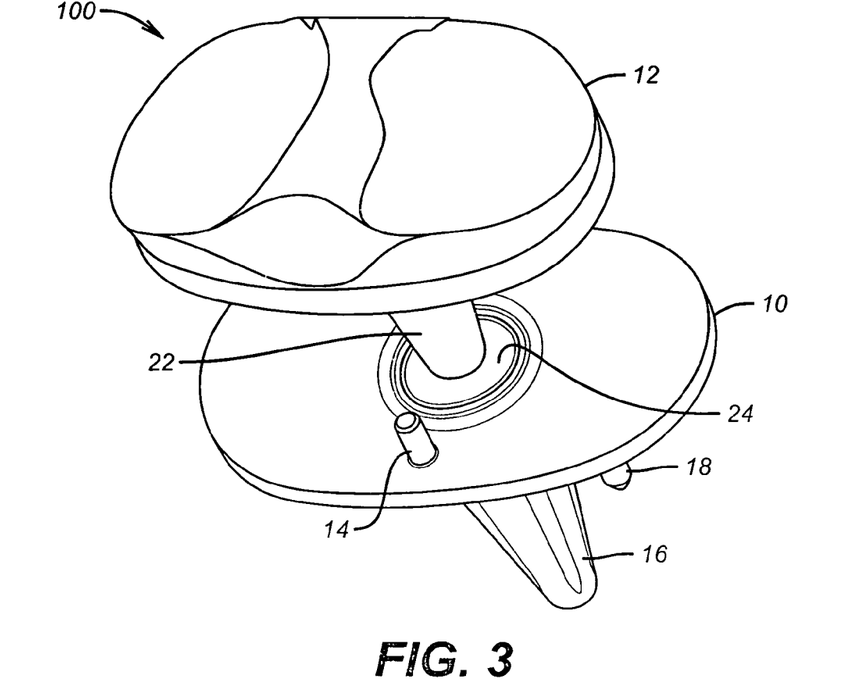
FIG. 3 is a perspective view of one embodiment of the present invention wherein a removable pin is installed in the base plate.

FIGS. 1-4 are various views of an insert/tibia base plate system 100 in accordance with one embodiment of the present invention. As shown in FIG. 1, the device 100 is comprised of a base plate 10, an insert 12 and a pin 14. In the depicted embodiment, the pin 14 is adapted to engage a portion of the base plate 10 and the insert 12, to thereby prevent rotation between the insert 12 and the base plate 10. More specifically, in the embodiment depicted in FIGS. 1-4, the pin 14 is adapted to be positioned in the opening 20 in the base plate while a portion of the pin 14 extends into an opening 28 (see FIG. 2) formed in the bottom surface 26 of the insert 12.

As will be recognized by those skilled in the art after a complete reading of the present application, the present invention may be employed with any of a variety of different types of tibia insert/tibia base plate combinations. In the depicted embodiment, the tibia base plate is comprised of a stem 16 and a plurality of pegs 18. The stem 16 is adapted to be positioned in the medullary canal of a patient's tibia after the end of the tibia has been resected. The pegs 18 (typically there are four such pegs on a base plate) are also adapted to be positioned in the tibia. The base plate 10 has an opening 24 that is adapted to receive a cone 22 formed on the insert 12. The base plate 10 may be made of any of a variety of different types of biologically compatible metals, e.g., cobalt chrome. The insert 12 may be made of a wear resistance material, such as ultra high molecular weight polyethylene (UHMWPE) material or a highly cross-linked material. Similarly, the pin 14 may be made of a variety of different materials, such as a metal or polyethylene. In one particular embodiment, the pin 14 may be made of cobalt chrome.

In general, in accordance with the present invention, the removable pin 14 allows a surgeon to select between a rotating or non-rotating tibia insert/tibia base plate system. More specifically, the pin 14 depicted in FIG. 1 is adapted to be readily removable or insertable into the opening 20 in the base plate 10 depending on the desires of the surgeon. For example, if it is desired to employ a non-rotating insert/tibia base plate system, the pin 14 would be employed to engage portions of the insert 12 and the base plate 10, e.g., the pin 14 may be positioned in the opening 20 and extend into the opening 28 in the insert 12. Conversely, if the surgeon desires to employ a rotating insert/tibia base plate system, then the pin 14 is omitted from the assembly. In some embodiments, the device 100 may be sold as a unit wherein the base plate 10, the insert 12 and pin 14 are sold as a single unit, and the pin 14 is installed in the opening 12. The pin 14 may be removably secured to the base plate 10 by any of a variety of known techniques. For example, the pin 14 may be press-fit, threaded or sintered into the opening 20 in the base plate 10. Thus, if the surgeon desires to use a non-rotating assembly, he may simply install the insert 12 on the base plate 10 having the pin 14 positioned therein. In contrast, if the insert/base plate assembly is supplied in the manner described above and if the surgeon wants to employ a rotating insert 12, then the surgeon need only remove the pin 14 from the base plate 10. Depending on the manner in which the pin 14 is secured to the base plate 10, it may be removed using a hammer, a hole punch or by unscrewing the threaded connection, or other techniques. Similarly, the opening 28 in the insert 12 and the pin 14 may be configured such that there is a press-fit or snap-fit between the portion of the pin 14 positioned in the opening 28 in the insert 12.

In general, it should be understood that the pin 14 may have any shape or desired configuration so long as it is structured to accomplish the purposes disclosed herein. For example, in the depicted embodiment in FIG. 1, the pin 14 has a generally circular configuration. However, the pin 14 could also have a non-circular configuration, e.g., a rectangular or square configuration or any polygon shape. Moreover, as used herein, the term "opening" should be understood to include any type of recess, groove, projection, indentation, slot, through-hole, or cavity that at least a portion of the pin 14 may be positioned in or engaged, in whole or in part. In the embodiment depicted in FIG. 1, the opening 20 in the base plate 10 is a circular hole having a counterbore recess 30 (see FIG. 4) formed therein. Similarly, the opening 28 in the bottom of the insert 12 is a generally circular hole. In view of the foregoing, it should be understood that the particular shape or configuration of the pin 14 as well as the shape and configuration of the opening 20 or the opening 28 should not be considered a limitation of the present invention unless such limitations are expressly set forth in the appended claims.

Figure 4:
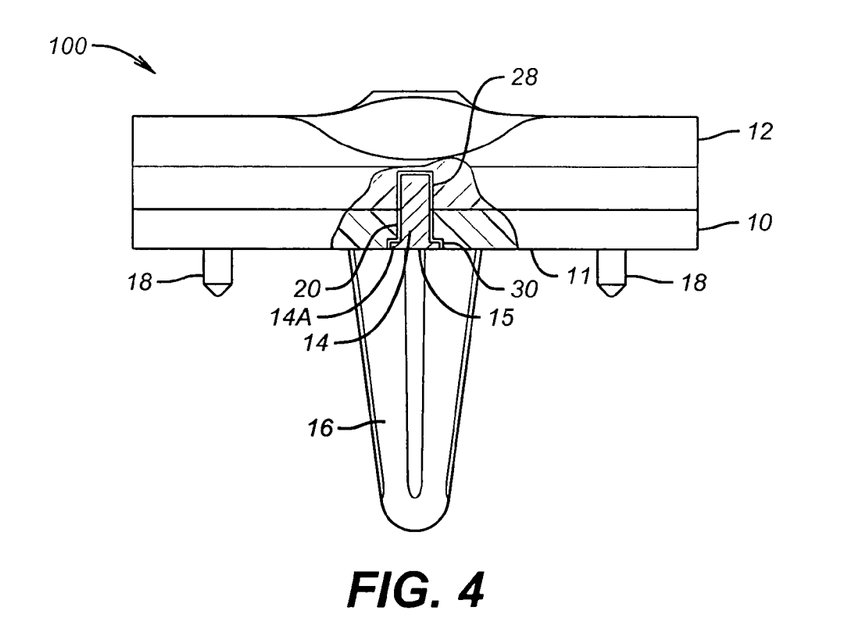
FIG. 4 is a partial cross-sectional view of one embodiment of the present invention in which the insert is non-rotatable relative to the tibia base plate.

FIG. 4 is a partial cross-sectional view of the device 100 wherein the insert 12 is prevented from rotating relative to the base plate 10 by the pin 14 positioned in the opening 20 and the opening 28. In the depicted embodiment, the pin 14 has a head 14a that is adapted to be positioned in the counterbore recess 30 formed in the base plate 10. In some cases, the device 100 may be configured such that the end surface 15 of the pin 14 is approximately flush with the bottom surface 11 of the base plate 10. In other embodiments, the end surface 15 of the pin 14 may extend slightly beyond the bottom surface 11 of the base plate 10.

The size of the pin 14 as well as the relative geometry between the various components, e.g., the insert 12, base plate 10 and the pin 14, may vary depending upon the particular application. For example, in the case where the pin 14 has a generally circular body, it may have a diameter that ranges from approximately ⅛"-³⁄₁₆" (3.2-4.8 mm), and in one particular embodiment may have a diameter of approximately ⁵⁄₃₂" (3.97 mm). Similarly, the engagement between the pin 14 and the insert 12, the amount of the pin 14 that is positioned within the opening 28 in the insert 12 to thereby prevent rotation of the insert 12, may vary. For example, for some applications, the pin 14 may be sized or configured such that it extends approximately ⅛" into the opening 28 in the insert 12. In other cases, the pin 14 may be sized and configured such that it penetrates the entire thickness of the insert 12. In general, the pin 14 only need have sufficient engagement with the insert 12 and the base plate 10 to prevent rotation between the insert 12 and the base plate 10.

Figure 5A:
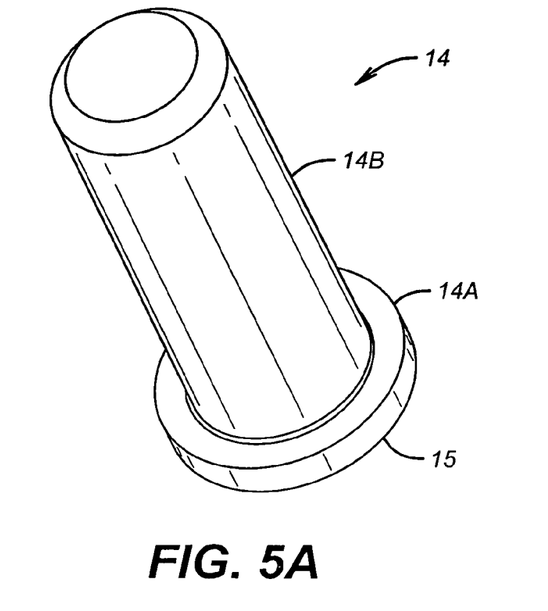
FIGS. 5A and 5B are depictions of various embodiments of a pin that may be employed with the present invention.
Figure 5B:
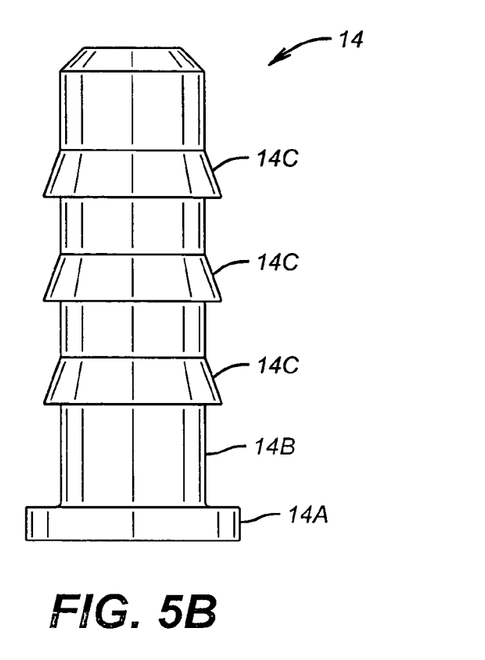

FIGS. 5A and 5B depict various illustrative embodiments of a pin 14 that may be employed with the inventions disclosed herein. As shown in FIG. 5A, the pin 14 has a head 14A, an end surface 15 and a generally smooth exterior surface 14B. In the embodiment shown in FIG. 5A, the pin 14 has a generally cylindrical configuration. As indicated previously, any desired configuration of the pin may be employed. FIG. 5B depicts the embodiment of the pin 14 when a plurality of ridges or barbs 14C are formed on the exterior surface 14B of the pin 14. The ridges 14C may be employed to more securely couple the pin 14 to the insert/base plate components 12, 10. Of course, other types of projections may be employed, e.g., splines, etc.

Figure 6:
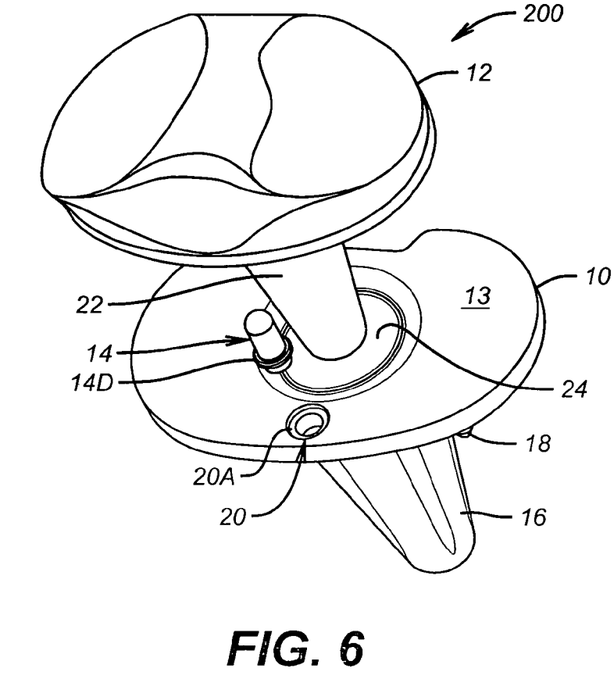
FIG. 6 is an exploded perspective view of another illustrative embodiment of an insert/tibia base plate system in accordance with the present invention.
Figure 7:
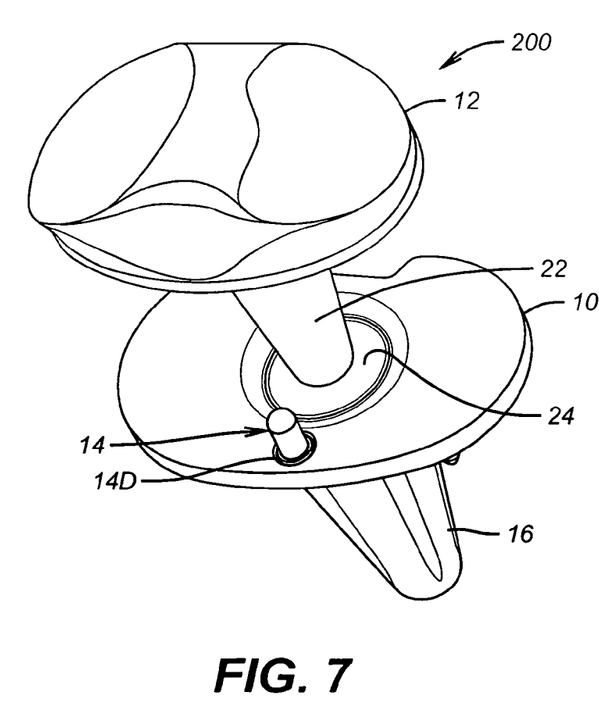
FIG. 7 is a perspective view of the device shown in FIG. 6 wherein an illustrative pin is positioned in the base plate shown therein.
Figure 8:
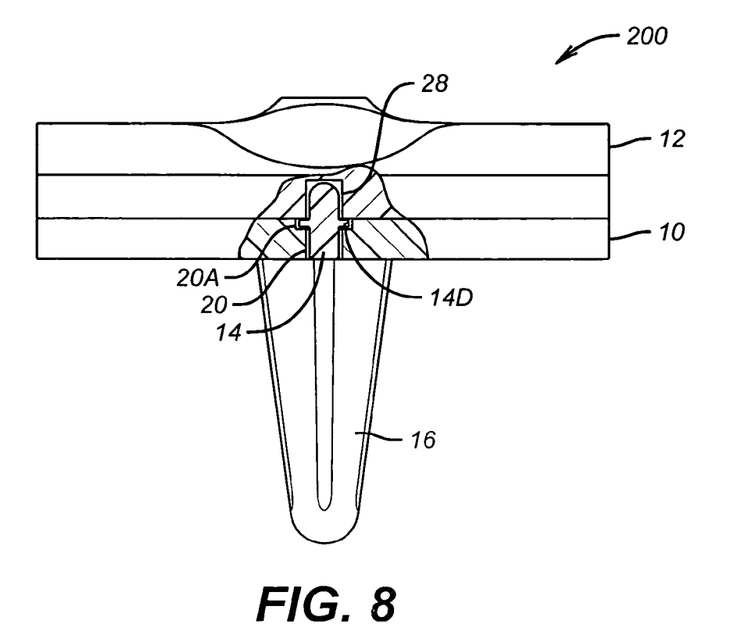
FIG. 8 is a partial cross-sectional view of another illustrative embodiment of the insert/tibia base plate system wherein the insert is prevented from rotating relative to the base plate.

FIGS. 6-8 depict yet another illustrative embodiment of a device 200 in accordance with the present invention. In the embodiment shown in these drawings, the pin 14 has an intermediate shoulder 14D that is adapted to engage a counterbore recess 20A formed in the top surface 13 of the base plate 10. That is, in this embodiment, the pin 14 is adapted to be installed from the top surface 13 of the base plate 10. As with the previous embodiment, a portion of the pin 14 is adapted to engage a portion of the insert 12, e.g., the pin 14 is adapted to be positioned in an opening 28 (not shown) in the bottom surface of the insert 12. FIG. 7 depicts the device 200 when the pin 14 is positioned in the opening 20 in the base plate 10, and the cone 22 of the insert 12 is ready to be positioned in the opening 24 in the stem 16. FIG. 8 is a partial cross-sectional view of the device 200 depicting the pin 14, with the intermediate shoulder 14D, positioned in the opening 20 and in the opening 28 formed in the insert 12. As with the previous embodiment, the pin 14 engages at least a portion of the insert 12 and the base plate 10 to thereby prevent relative rotation between the insert 12 and the base plate 10. The size, shape and configuration of the pin 14 as well as the openings 20, 28 may vary depending upon the particular application.

Figure 9:
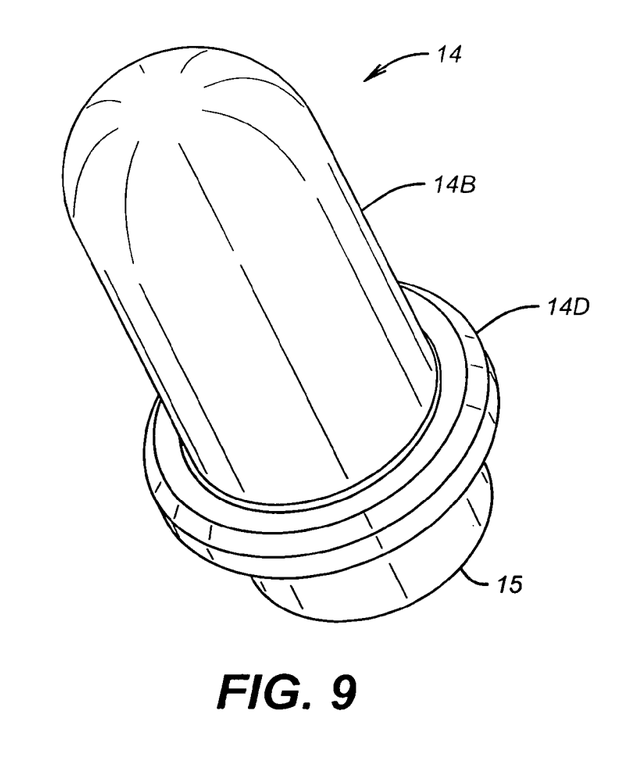
FIG. 9 is a depiction of one illustrative embodiment of a pin that may be employed with the device shown in FIG. 8.

FIG. 9 is a depiction of an illustrative embodiment of a pin 14 that may be employed with the device 200 depicted in FIGS. 6-8. As shown therein, the pin 14 has a relatively smooth cylindrical exterior surface 14B and a shoulder 14D that is formed at some location between the ends of the pin 14. As mentioned above, the size, shape and configuration of the pin 14 shown in FIG. 9 may vary depending upon the particular application.

Figure 10A:
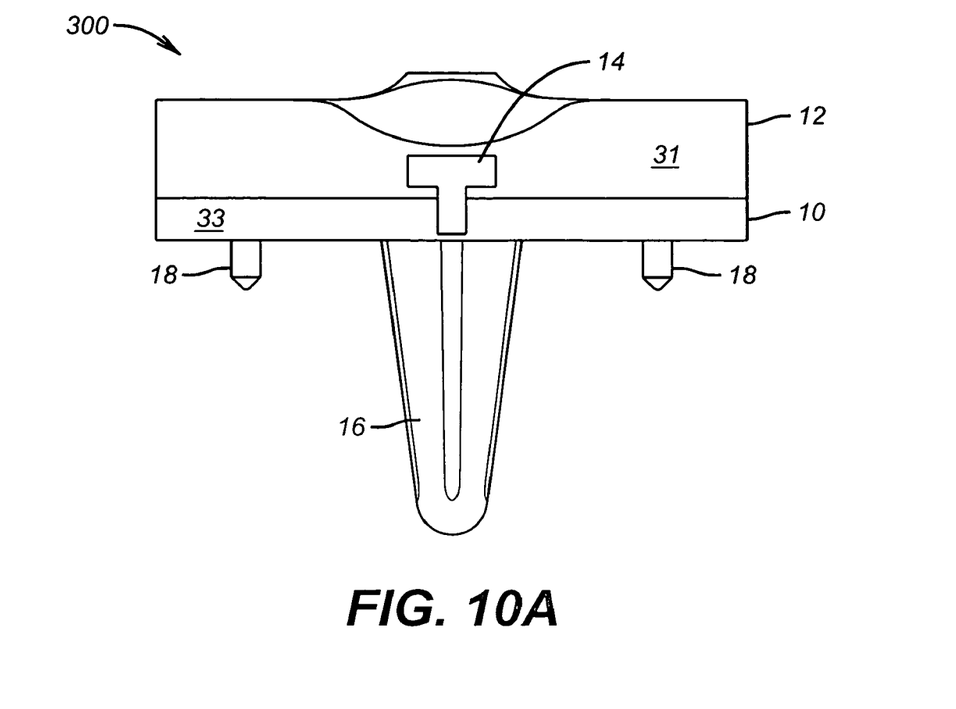
FIGS. 10A-10D are various views of yet another illustrative embodiment of an insert/tibia base plate system in accordance with the present invention.
Figure 10B:
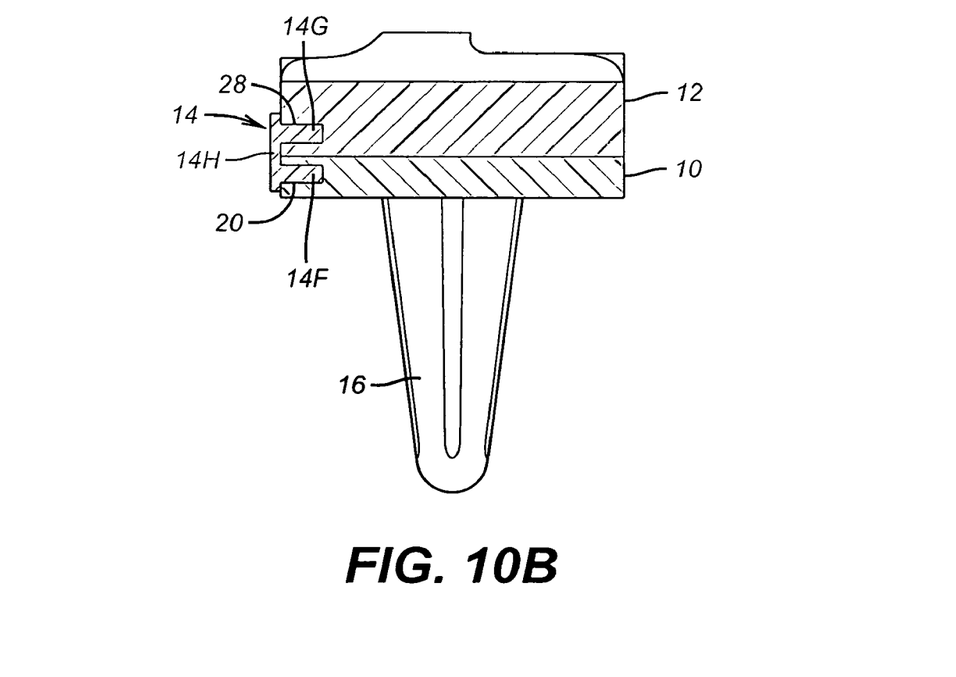
Figure 10C:
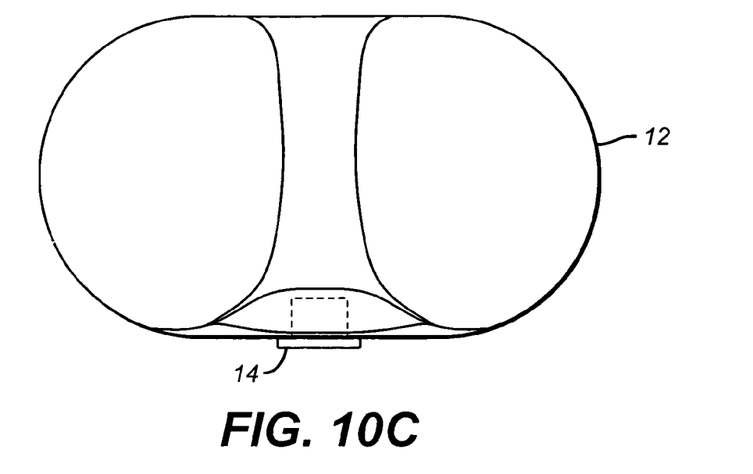
Figure 10D:
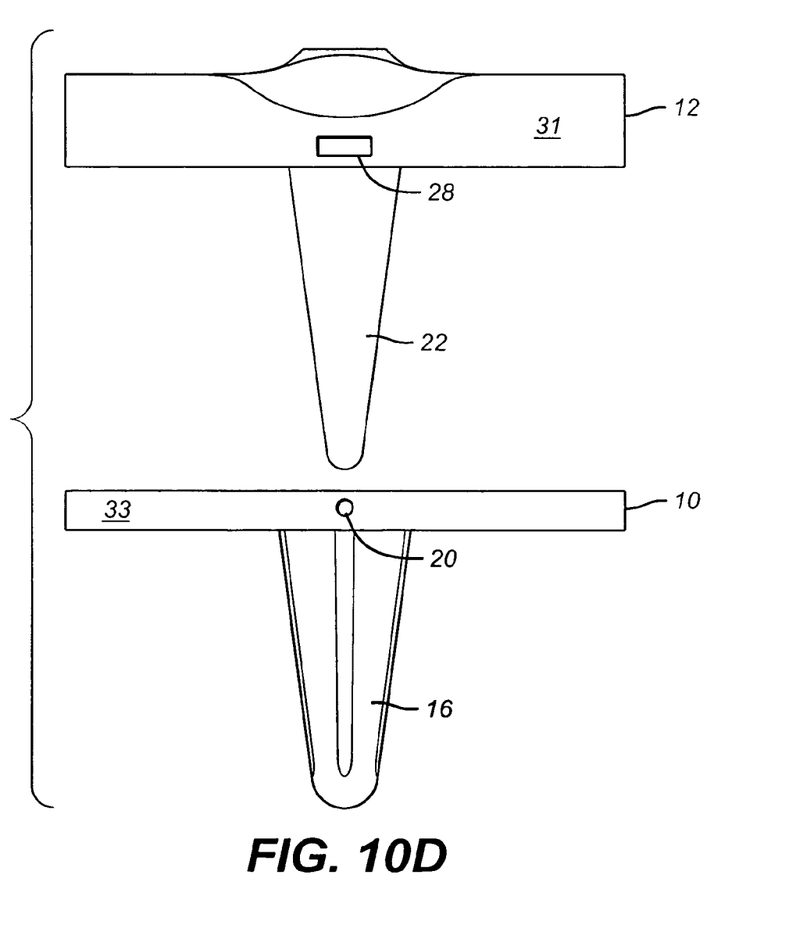

FIGS. 10A-10D depict yet another illustrative embodiment of a device 300 in accordance with the present invention. As shown therein, the device 300 comprises a base plate 10, an insert 12 and a pin 14. The pin 14 is configured to engage at least a portion of the insert 12 and the base plate 10 to thereby prevent relative rotation between the two components. More specifically, in the depicted embodiment, the pin 14 is configured so as to engage openings 28, 20 (see FIG. 10B) that are formed in the side surfaces 31, 33 of the insert 12 and the base plate 10, respectively. In the depicted embodiment, the pin 14 has a generally T-shaped configuration when viewed from the front (see FIG. 10A). More specifically, as shown in FIG. 10B, the pin 14 has tabs 14F and 14G that are adapted to engage the openings 20 and 28, respectively.

Figure 11A:
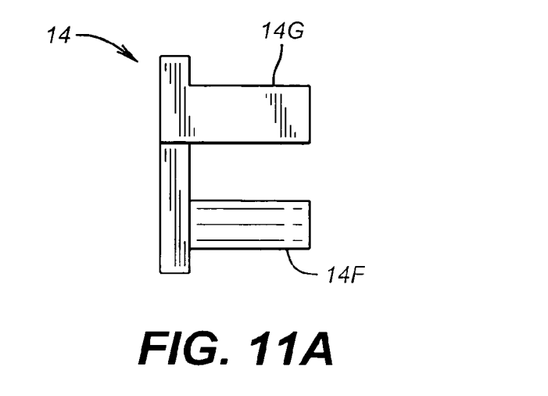
FIGS. 11A-11C are various views of an illustrative pin that may be employed with the embodiment depicted in FIGS. 10A-10D.
Figure 11B:
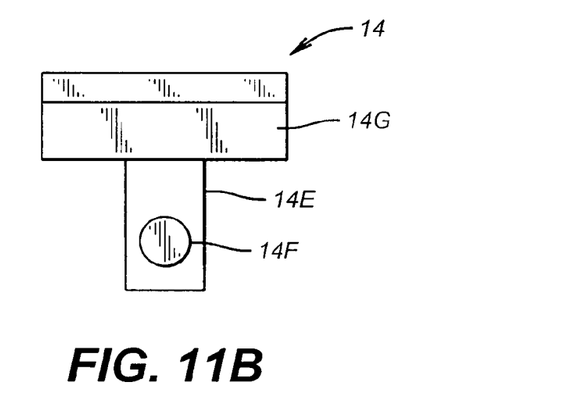
Figure 11C:
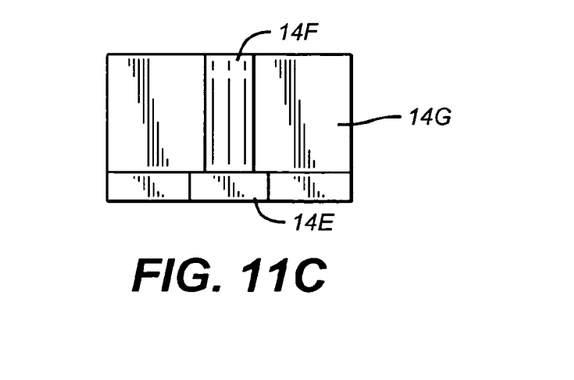

FIGS. 11A-11C are various views of the pin 14 depicted in FIGS. 10A-10B. As shown therein, in the depicted embodiment, the pin 14 is comprised of a vertical member 14E and the tabs 14F and 14G. In one illustrative embodiment, the tab 14F is a generally cylindrical projection that is adapted to engage the generally cylindrical opening 20 (see FIG. 10D) in the side surface 33 of the base plate 10. The tab 14G is a generally rectangular projection that is adapted to engage the generally rectangular opening 28 (see FIG. 10D) formed in the side surface 31 of the insert 12. The tabs 14F, 14G are sized and configured such that they may be press-fit or snap-fit with the openings 20, 28 in the base plate 10, insert 12, respectively. Moreover, it should be understood that the tabs 14F, 14G, as well as the openings in which they are to be positioned, may be configured in any desired manner. For example, the pin 14 may be configured such that the generally circular tab 14F is adapted to be positioned in a generally circular opening formed in the side surface 31 of the insert 12, whereas the generally rectangular tab 14G may be adapted to fit in a generally rectangular opening formed in the side surface 33 of the base plate 10. Lastly, the pin 14 depicted in FIGS. 10A-10D may also be configured such that both the tabs 14F and 14G are generally circular or they are both generally rectangular. As should be clear from the foregoing, there is a vast variety of possible combinations and configurations of the pin 14 that may be employed with the embodiment shown in FIGS. 10A-10B as well as with the other embodiments of the invention disclosed herein.

In the depicted embodiment (see FIG. 10B), the pin 14 has an outer surface 14h that is not flush with the side surfaces 31 and 33 of the insert 12 and base plate 10, respectively. However, such a flush mounting arrangement could be readily accomplished if desired. Moreover, it should be noted that the pin 14 depicted in FIGS. 10A-10D is located on a front or anterior portion of the device 300. This positioning is useful in that the surgeon has the most ready access to the front portion of a knee during the surgical process and inserting or removing the pin 14 may be the last operation performed prior to closing the surgical site. Additionally, if it is desired to later insert or remove a pin 14 into or from the insert/base plate assembly, then minimally invasive surgical techniques may be employed to access the pin 14 depicted in the various embodiments described herein.

The present invention is directed to a rotating/non-rotating tibia base plate/insert system. In one illustrative embodiment, the device comprises a tibia base plate, an insert adapted to be positioned above the base plate, and at least one removable pin that, when installed, engages at least a portion of the insert and the base plate to thereby prevent relative rotation between the insert and the base plate.

In another illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate.

In yet another illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate, wherein the pin has a head that is positioned adjacent a bottom surface of the base plate.

In a further illustrative embodiment, the device comprises a tibia base plate having an opening formed therein, an insert adapted to be positioned above the base plate, the insert having an opening formed therein, and at least one removable pin that, when installed, engages the opening in the base plate and the opening in the insert to thereby prevent relative rotation between the insert and the base plate, wherein the pin has a shoulder that is positioned adjacent a top surface of the base plate.

In still a further illustrative embodiment, the device comprises a tibia base plate, the plate having an opening formed in a side surface of the base plate, an insert adapted to be positioned above the base plate, the insert having an opening formed on a side surface of the insert, and at least one removable pin that, when installed, prevents relative rotation between the insert and the base plate, wherein a first portion of the pin is configured to engage the opening formed in the side surface of the base plate and a second portion of the pin is configured to engage the opening formed in the side surface of the insert.

In yet a further illustrative embodiment, the device comprises a tibia base plate, an insert adapted to be positioned above the base plate, and a removable means for preventing relative rotation between the insert and the base plate. In some embodiments of the present invention, the removable means for preventing relative rotation between the insert and the base plate comprises at least one removable pin that, when installed, engages at least a portion of the insert and the base plate to thereby prevent relative rotation between the insert and the base plate.

In one illustrative embodiment of the present invention, the method comprises obtaining a prosthetic knee assembly comprised of a tibia base plate, a tibia insert and a removable pin, the assembly being adapted to be configured in a first state such that the tibia insert may rotate relative to the base plate or in a second state such that said tibia insert cannot rotate relative to said base plate, making at least one incision adjacent a patient's knee, installing the prosthetic knee assembly in the patient, wherein the removable pin is removed such that the assembly is in the first state wherein the tibia insert may rotate relative to the tibia base plate, and closing the incision.

In another illustrative embodiment, the method comprises obtaining a prosthetic knee assembly comprised of a tibia base plate, a tibia insert and a removable pin, the assembly being adapted to be configured in a first state such that the tibia insert may rotate relative to the base plate or in a second state such that said tibia insert cannot rotate relative to said base plate, making at least one incision adjacent a patient's knee, installing the prosthetic knee assembly in the patient, wherein the removable pin is left in place such that the assembly is in the second state wherein the tibia insert cannot rotate relative to the tibia base plate, and closing the incision.

In yet another illustrative embodiment, the method comprises providing a tibia base plate having a removable pin positioned in an opening formed in the tibia base plate, positioning the tibia base plate on a tibia of a patient, and positioning a tibia insert above the tibia base plate, wherein at least a portion of the removable pin is positioned in an opening formed in the tibia insert to thereby prevent relative motion between the tibia insert and the tibia base plate.

In a further illustrative embodiment, the method comprises providing a tibia base plate having a removable pin positioned in an opening formed in the tibia base plate, positioning the tibia base plate on a tibia of a patient, positioning a tibia insert above the tibia base plate and, before or after the tibia base plate is positioned on the tibia of the patient, removing the removable pin to thereby allow relative motion between the tibia insert and the tibia base plate.

In yet a further illustrative embodiment, the method comprises providing a tibia base plate having an opening formed in a side surface of the tibia base plate, positioning the tibia base plate on a tibia of a patient, positioning a tibia insert above the tibia base plate, the tibia insert having an opening formed in a side surface of the tibia insert, and positioning at least a portion of a removable pin in the opening in the side surface of the tibia base plate and another portion of the removable pin in the side surface of the tibia insert to thereby prevent relative motion between the tibia insert and the tibia base plate.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A device, comprising:
a first tibia base plate comprising an upper surface, a lower surface and an outer perimeter side surface extending between said upper surface and said lower surface of said first tibia base plate;
an insert comprising an upper surface, a lower surface and an outer perimeter side surface extending between said upper surface and said lower surface of said insert, said insert adapted to be positioned above said first base plate, said insert and said first base plate having a first configuration, wherein said insert is translationally fixed to said first base plate and rotatable relative to said first base plate;
a connector rotatably connecting said insert to said first tibia base plate; and
at least one removable pin having a first portion and a second portion, said first portion of said pin sized for engagement with an opening formed in said outer perimeter side surface of said first base plate and said second portion of said pin sized for engagement with an opening formed in said outer perimeter side surface of said insert to thereby prevent relative rotation between said insert and said first base plate.

2. The device of claim 1, wherein said first base plate is comprised of a metal.

3. The device of claim 1, wherein said insert is comprised of a nonmetallic material.

4. The device of claim 1, wherein at least a portion of said pin is secured in an opening in said first base plate by at least one of a press-fit connection, a threaded connection, and a sintered connection.

5. The device of claim 1, wherein said pin has an outer surface that is substantially flush with said outer perimeter side surface of one of said first base plate and said insert.

6. The device of claim 1, wherein said openings in said first tibia base plate and said insert are formed on anterior portions of said outer perimeter side surfaces of said first base plate and said insert, respectively.

7. The device of claim 1, wherein said pin has at least one of a circular, rectangular and square cross-sectional configuration.

8. The device of claim 1, wherein said pin has a smooth exterior surface.

9. The device of claim 1, wherein said pin has at least one projection formed on an exterior surface of said pin.

10. The device of claim 1, wherein said pin is comprised of a metal.

11. A device, comprising:
- a first tibia base plate comprising an upper surface, a lower surface and an outer perimeter side surface extending between said upper surface and said lower surface of said first tibia base plate;
- an insert comprising an upper surface, a lower surface and an outer perimeter side surface extending between said upper surface and said lower surface of said insert, said insert adapted to be positioned above said first base plate, said insert and said first base plate having a first configuration, wherein said insert is translationally fixed to said first base plate and rotatable relative to said first base plate;
- a means for rotatably connecting said insert to said first tibia base plate; and
- a removable means for selective engagement with both said insert and said first tibia base plate for preventing relative rotation between said insert and said first base plate, wherein, when installed, a first portion of said removable means is configured to engage an opening formed in said outer perimeter side surface of said first base plate and a second portion of said removable means is configured to engage an opening formed in said outer perimeter side surface of said insert to thereby prevent relative rotation between said insert and said first base plate.

12. The device of claim 11, wherein said removable means for preventing relative rotation between said insert and said first base plate comprises a removable pin.

13. The device of claim 11, wherein said first base plate is comprised of a metal.

14. The device of claim 11, wherein said insert is comprised of a nonmetallic material.

15. The device of claim 11, wherein said removable means for preventing relative rotation between said insert and said first base plate has an outer surface that is substantially flush with said outer perimeter side surface of one of said first base plate and said insert.

16. The device of claim 11, wherein at least a portion of said removable means for preventing relative rotation between said insert and said first base plate is secured in an opening in said first base plate by at least one of a press-fit connection, a threaded connection, and a sintered connection.

17. The device of claim 11, wherein said openings in said first tibia base plate and said insert are formed on anterior portions of said outer perimeter side surfaces of said first base plate and said insert, respectively.

18. The device of claim 11, wherein said removable means for preventing relative rotation between said insert and said first base plate has at least one of a circular, rectangular and square cross-sectional configuration.

19. The device of claim 11, wherein said removable means for preventing relative rotation between said insert and said first base plate has a smooth exterior surface.

20. The device of claim 11, wherein said removable means for preventing relative rotation between said insert and said first base plate has at least one projection formed on an exterior surface of said removable means.

21. The device of claim 11, wherein said removable means for preventing relative rotation between said insert and said first base plate is comprised of a metal.

* * * * *